US005693640A

United States Patent [19]
Ladduwahetty et al.

[11] Patent Number: 5,693,640
[45] Date of Patent: Dec. 2, 1997

[54] PYRIDAZINO-INDOLE DERIVATIVES

[75] Inventors: Tamara Ladduwahetty, London; Angus Murray MacLeod, Bishops Stortford, both of United Kingdom

[73] Assignee: Merck, Sharp & Dohme, Ltd., Hoddesdon, England

[21] Appl. No.: 470,773

[22] Filed: Jun. 6, 1995

[30] Foreign Application Priority Data

Jun. 15, 1994 [GB] United Kingdom ............... 9411955

[51] Int. Cl.$^6$ .................. A61K 31/50; C07D 487/04
[52] U.S. Cl. ............... 514/248; 544/233; 544/234; 548/492
[58] Field of Search ............... 544/234; 514/248

[56] References Cited

U.S. PATENT DOCUMENTS 5,599,814  2/1997  Bare et al. ............... 544/234

FOREIGN PATENT DOCUMENTS 0 512 817 A1  11/1992  European Pat. Off. .

OTHER PUBLICATIONS

Choi, *Neuron* 1, pp. 623–634 (1988).
Koh et al, *Brain Research*, 533, pp. 315–320 (1990).
Trujillo et al, *Science* 251, pp. 85–87 (1991).

*Primary Examiner*—Emily Bernhardt
*Attorney, Agent, or Firm*—Robert J. North; Melvin Winokur

[57] ABSTRACT

A class of pyridazino[4,5-b]indole-1,4-dione derivatives, substituted in the 2-position by an optionally substituted phenyl moiety, are selective non-competitive antagonists of NMDA receptors and/or are antagonists of AMPA receptors, and are therefore of utility in the treatment and/or prevention of conditions, such as neurodegenerative disorders, convulsions or schizophrenia, which require the administration of an NMDA and/or AMPA antagonist.

4 Claims, No Drawings

PYRIDAZINO-INDOLE DERIVATIVES

This invention relates to a class of pyridazino[4,5-b]indole-1,4-dione derivatives which are substituted in the 2-position by an optionally substituted phenyl moiety. These compounds are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, *Neuroscience Lett.*, 1991, 121, 263; Murray et al., *Pain*, 1991, 44, 179; and Woolf and Thompson, *Pain*, 1991, 44, 293), antidepressant (see, for example, Trullas and Skolnick, *Eur. J. Pharmacol.*, 1990, 185, 1) and anxiolytic (see, for example, Kehne et al., *Eur. J. Pharmacol.*, 1991, 193, 283) effects, and the compounds of the present invention may accordingly be useful in the management of pain, depression and anxiety.

The association of NMDA receptor antagonists with regulation of the nigrostriatal dopaminergic system has recently been reported (see, for example, Werling et al., *J. Pharmacol. Exp. Ther.*, 1990, 255, 40; Graham et al., *Life Sciences*, 1990, 47, PL-41; and Turski et al., *Nature (London)*, 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., *Journal of Cerebral Blood Flow and Metabolism*, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalk-3-ene carboxylic acids and esters described in EP-A-0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., *Br. J. Pharmacol.*, 1990, 101, 776) and AIDS (cf. Lipton et al., *Society for Neuroscience Abstracts*, 1990, 16, 128.11).

NMDA antagonists have, moreover, been shown to have an effect on the neuroendocrine system (see, for example, van den Pol et al., *Science*, 1990, 250, 1276; and Urbanski, *Endocrinology*, 1990, 127, 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region oft he forebrain possessing dopamine-sensitive neurones) is well known to exist (see, for example, *J. Neurochem.*, 1985, 45, 477). It is also well known that dopaminergic transmission in the striatum is modulated by glutamate (see, for example, *Neurochem. Int.*, 1983, 5, 479), as also is the hyperactivity associated with presynaptic stimulation of the dopamine system by AMPA in the nucleus accumbens (cf. *Life Sci.*, 1981, 28, 1597). Compounds which are antagonists of AMPA receptors are therefore of value as neuroleptic agents.

EP-A-0512817 describes a class of fused pyridazinedione derivatives, including pyridazino[4,5-b]indole-1,4-diones, which are stated to function as excitatory amino acid antagonists and to be useful in the treatment of neurological disorders. There is, however, no disclosure nor any suggestion in EP-A-0512817 of substitution in the 2-position by an optionally substituted phenyl moiety.

The present invention accordingly provides a compound of formula I, or a salt or prodrug thereof:

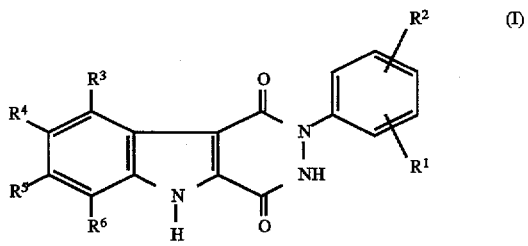

wherein $R^1$ and $R^2$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; or $R^1$ and $R^2$ together represent the residue of a carbocyclic or heterocyclic ring;

$R^3$, $R^4$, $R^5$ and $R^6$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

The invention also provides a pharmaceutical composition comprising a compound of formula I as defined above or a pharmaceutically acceptable salt thereof or a prodrug thereof in association with one or more pharmaceutically acceptable carriers and/or excipients.

The invention further provides a compound of formula I as defined above or a pharmaceutically acceptable salt thereof or a prodrug thereof for use in therapy.

In another aspect, the present invention provides the use of a compound of formula I as defined above or a pharmaceutically acceptable salt thereof or a prodrug thereof for the manufacture of a medicament for the treatment and/or prevention of conditions, in particular neurodegenerative disorders, which require the administration of a selective non-competitive antagonist of NMDA receptors.

In a further aspect, the present invention provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

In a still further aspect, the present invention provides a method for the treatment and/or prevention of conditions, in particular neurodegenerative disorders, which require the administration of a selective non-competitive antagonist of NMDA receptors, which method comprises administering to a patient in need of such treatment an effective amount of a compound of formula I as defined above or a pharmaceutically acceptable salt thereof or a prodrug thereof.

In a yet further aspect, the present invention provides a method for the treatment and/or prevention of conditions, such as schizophrenia, which require the administration of an antagonist of AMPA receptors, which method comprises administering to a patient in need of such treatment an effective amount of a compound of formula I as defined above or a pharmaceutically acceptable salt thereof or a prodrug thereof.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups. A particular aryl($C_{1-6}$)alkyl group is benzyl.

A particular aryl($C_{2-6}$)alkenyl group is phenylethenyl.

A particular aryl($C_{2-6}$)alkynyl group is phenylethynyl.

Suitable heterocycloalkyl groups include piperidyl, piperazinyl and morpholinyl groups.

A particular heterocycloalkyl($C_{1-6}$)alkyl group is morpholinylethyl.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl, pyrrolyl, indolyl, furyl, benzofuryl, thienyl, benzthienyl and oxadiazolyl.

Particular heteroaryl($C_{1-6}$)alkyl groups include pyridylmethyl, pyrrolylmethyl, indolylmethyl, furylmethyl and thienylmethyl.

Where $R^1$ and $R^2$ together represent the residue of a carbocyclic or heterocyclic ring, the ring may be saturated or unsaturated. The ring may suitably be a 4- to 9-membered ring, but will preferably be a 5- or 6-membered ring. Where $R^1$ and $R^2$ together represent the residue of a heterocyclic ring, this ring may contain up to four heteroatoms selected from oxygen, nitrogen and sulphur. Suitable carbocyclic rings of which $R^1$ and $R^2$ together represent the residue include cyclohexane, cyclohexene, cyclohexadiene and benzene rings. Suitable heterocyclic rings of which $R^1$ and $R^2$ together represent the residue include dioxolane, dioxane, pyridine, furan, thiophene, pyrrole, thiazole and thiadiazole rings.

The hydrocarbon and heterocyclic groups, as well as the carbocyclic or heterocyclic ring completed by $R^1$ and $R^2$, may in turn be optionally substituted by one or more groups selected from $C_{1-6}$ alkyl, adamantyl, phenyl, halogen, $C_{1-6}$ haloalkyl, morpholinyl($C_{1-6}$)alkyl, trifluoromethyl, hydroxy, $C_{1-6}$ alkoxy, $C_{1-6}$ alkoxy($C_{1-6}$)alkyl, $C_{1-6}$ alkoxy($C_{1-6}$) alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Suitable values for the substituents $R^1$ and $R^2$ include $C_{1-6}$ alkyl, aryl, aryl($C_{1-6}$)alkyl, aryl($C_{2-6}$)alkenyl, aryl($C_{2-6}$) alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, arylthio, arylsulphonyl, arylamino, aryl($C_{1-6}$)alkylamino, di($C_{1-6}$) alkylamino, arylcarbonylamino, arylcarbonyl or heteroarylcarbonyl, any of which groups may be optionally substituted; and hydrogen, halogen, trifluoromethyl or nitro. Examples of optional substituents on the groups $R^1$ and/or $R^2$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values for the substituents $R^1$ and $R^2$ include hydrogen, methyl, phenyl, benzyl, methoxymethyl-benzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methylallyloxy, phenoxy, methyl-phenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, one or both of $R^1$ and $R^2$ represent hydrogen.

Where $R^1$ and $R^2$ together represent the residue of a carbocyclic or heterocyclic ring, this may be, in particular, a dioxolane or optionally substituted benzene ring.

The benzo moiety of the fused tricyclic ring system shown in formula I above may be substituted or unsubstituted. Particular substituents include halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio and $C_{2-7}$ alkoxycarbonyl. Suitably $R^6$ is hydrogen and $R^3$, $R^4$ and $R^5$ independently represent hydrogen, halogen, cyano, trifluoromethyl, nitro, $C_{1-6}$ alkyl or $C_{2-6}$ alkenyl, at least one of $R^3$, $R^4$ and $R^5$ desirably being other than hydrogen. Preferably, $R^4$ and $R^6$ each represents hydrogen and $R^3$ and $R^5$ independently represent hydrogen, cyano, trifluoromethyl, nitro, methyl, ethyl, vinyl or halogen, especially chlorine or iodine. In a particular embodiment, $R^5$ represents hydrogen, cyano, trifluoromethyl, nitro or halogen, especially chlorine; and $R^3$ is hydrogen or ethyl.

For use in medicine, the salts of the compounds of formula I will be pharmaceutically acceptable salts. Other salts may, however, be useful in the preparation of the compounds according to the invention or of their pharmaceutically acceptable salts.

Suitable pharmaceutically acceptable salts of the compounds of formula I above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, add addition salts may, for example, be formed by mixing a solution of the compound according to the invention with a solution of a pharmaceutically acceptable acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

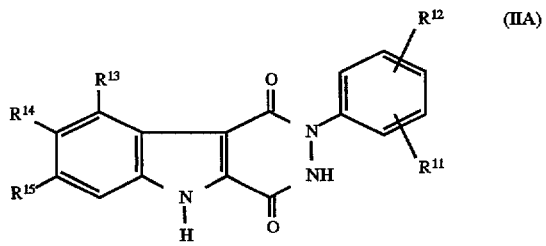

(IIA)

wherein
$R^{11}$ and $R^{12}$ independently represent $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; or $R^{11}$ and $R^{12}$ together represent the residue of a carbocyclic or heterocyclic ring; and
$R^{13}$, $R^{14}$ and $R^{15}$ independently represent hydrogen, halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

In one embodiment of the compounds of formula IIA above, $R^{15}$ represents halogen, cyano, trifluoromethyl, nitro, hydroxy, amino, carboxy, $C_{1-6}$ alkyl, $C_{2-6}$ alkenyl, $C_{1-6}$ alkoxy, $C_{1-6}$ alkylthio or $C_{2-7}$ alkoxycarbonyl.

Examples of optional substituents on the groups $R^{11}$ and/or $R^{12}$ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$) alkylamino.

Particular values of $R^{11}$ and/or $R^{12}$ with respect to formula IIA include hydrogen, methyl, phenyl, benzyl, methoxymethyl-benzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methyl-phenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, at least one of $R^{11}$ and $R^{12}$ represents hydrogen. In a particular embodiment, one of $R^{11}$ and $R^{12}$ is hydrogen and the other is hydrogen or phenoxy.

Suitably, $R^{13}$ represents hydrogen, nitro, methyl, ethyl, vinyl or halogen, especially chlorine or iodine. Preferably, $R^{13}$ is hydrogen, ethyl, chlorine or iodine.

Suitably, $R^{14}$ represents hydrogen or chlorine, preferably hydrogen.

Suitably, $R^{15}$ represents hydrogen, cyano, trifluoromethyl, nitro, methyl or halogen, preferably hydrogen or chlorine.

Specific compounds within the scope of the present invention include:
2-phenylpyridazino[4,5-b]indole-1,4-dione;
and salts and prodrugs thereof.

The pharmaceutical compositions according to the invention are preferably in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurodegeneration, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds according to the present invention may be prepared by a process which comprises cyclising a compound of formula III:

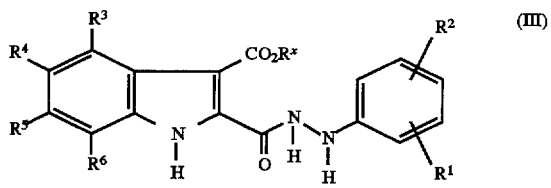

wherein $R^1$, $R^2$, $R^3$, $R^4$, $R^5$ and $R^6$ are as defined above, and $R^x$ represents $C_{1-4}$ alkyl.

The cyclisation is conveniently effected by heating compound III in the presence of a strong base. Suitably, the base is an alkali metal alkoxide, in which case the reaction is advantageously carried out in the corresponding alkanol as solvent. In a typical procedure, the cyclisation is effected in the presence of sodium methoxide, in methanol at reflux.

The intermediates of formula III above may be prepared by reacting a compound of formula IV with the appropriate phenylhydrazine derivative of formula V:

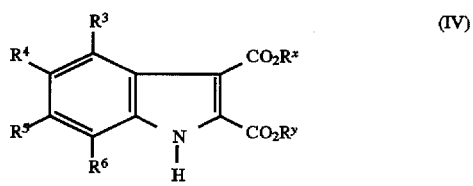

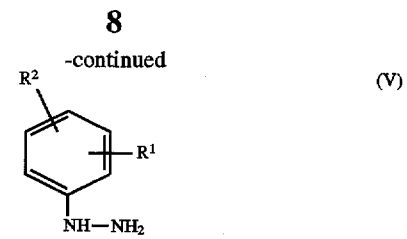

wherein $R^1$, $R^2$, $R^3$, $R^4$, $R^5$, $R^6$ and $R^x$ are as defined above, and $R^y$ represents $C_{1-4}$ alkyl.

Suitable values for the substituents $R^x$ and $R^y$ include methyl and ethyl, especially methyl.

The reaction between compounds IV and V is suitably effected by heating the reagents together in a suitable solvent, for example a lower alkanol such as ethanol, advantageously at reflux. The required intermediate of formula III may be isolated as such from the reaction mixture, or cyclised in situ as described above to afford the desired product of formula I.

The starting materials of formula IV may typically be prepared by procedures analogous to those described in EP-A-0512817.

Where they are not commercially available, the reagents of formula V may suitably be prepared by standard methods well known from the art.

It will be appreciated that any compound of formula I initially obtained from the above process may, where appropriate, subsequently be elaborated into a further desired compound of formula I using techniques known from the art.

Where the above-described process for the preparation of compounds of use in the invention gives rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Example illustrates the preparation of compounds of use in the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of use in the invention on responses to NMDA and AMPA can be assessed using the rat cortical slice as described by Wong et al., *Proc. Natl. Acad.*

*Sci. USA*, 1986, 83, 7104. The apparent equilibrium constant ($K_b$) is calculated from the righthand shift in the NMDA or AMPA concentration-response curves produced by the compound under test. The compound of accompanying Example 1 was tested and was found to possess a $K_b$ value in response to NMDA of below 150 µm.

Binding Studies

The ability of test compounds to displace $^3$H-L-689,560 (trans-2-carboxy-5,7-dichloro-4-phenylaminocarbonylamino-1,2,3,4-tetrahydroquinoline) binding to the strychnine-insensitive site present on the NMDA receptor of rat forebrain membranes can be determined by the method of Grimwood et al., *Proceedings of the British Pharmacological Society*, July 1991, Abstract C78. The concentration of the compound of accompanying Example 1 required to displace 50% of the specific binding ($IC_{50}$) is below 50 µM.

EXAMPLE 1

2-Phenylpyridazino[4,5-b]indole-1,4-dione a) 3-Methoxycarbonylindole-2-(2'-phenyl) carbohydrazide Dimethyl indole-2,3-dicarboxylate (200 mg) was heated in phenylhydrazine (1 ml) at 140° C. for 2 hours. The mixture was diluted with $CH_2Cl_2$ and washed with aqueous citric acid solution, dried, concentrated and triturated with $Et_2O$ to give the title compound. $^1$H nmr (250MHz, $d_6$-DMSO) δ 3.97 (3H, s), 6.76 (1H, t, J=7Hz), 6.68 (2H, d, J=7.5Hz), 7.19 (2H, t, J=7.5Hz), 7.25–7.36 (2H, m), 7.57 (1H, d, J=7Hz), 8.11 (1H, d, J=7Hz), 8.21 (1H, d, J=3Hz), 11.58 (1H, d, J=3Hz) and 12.72 (1H, s).

b) 2-Phenylpyridazino[4,5-b]indole-1,4-dione

Sodium (0.150 g, 6.5 mmol) was dissolved in anhydrous MeOH and 3-methoxycarbonylindole-2-(2'-phenyl) carbohydrazide (0.200 g, 0.65 mmol) added as a solution in MeOH at 25° C. The reaction mixture was heated to reflux for 0.5 hours. The reaction mixture was cooled and the MeOH evaporated. The residue was dissolved in $H_2O$ (10 ml) and acidified to pH2. The aqueous layer was extracted with EtOAc and the organic layer dried over $MgSO_4$ and evaporated. The resulting solid was recrystallized from MeOH/EtOAc to give the title compound, $^1$H nmr (360MHz, $d_6$-DMSO) δ 8.19 (1H, d, J=7.2Hz), 7.63 (3H, m), 7.48 (3H, m), 7.35 (2H, q, J=7.2Hz, 14.4Hz). MS (CI$^+$) m/z 278 (M+1)$^+$.

We claim:

1. A compound of formula I, or a pharmaceutically acceptable salt thereof:

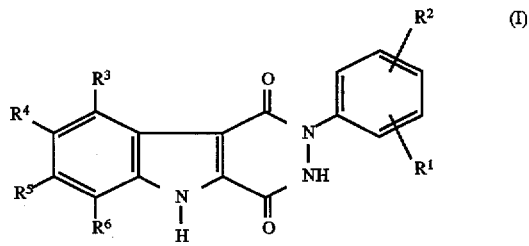

wherein $R^1$ and $R^2$ represent hydrogen;

$R^3$ represents hydrogen or ethyl;

$R^4$ and $R^6$ represent hydrogen; and $R^5$ represents hydrogen, halogen, cyano, trifluoromethyl, or nitro.

2. A compound as claimed in claim 1 selected from: 2-phenylpyridazino[4,5-b]indole-1,4-dione; or a pharmaceutically acceptable salt thereof.

3. A pharmaceutical composition comprising a compound as claimed in claim 1 in association with a pharmaceutically acceptable carrier.

4. A method for the treatment of stroke, epilepsy, cerebral ischaemia, anoxia or hypoglycemia, which require the administration of a selective non-competitive antagonist of NMDA receptors, which comprises administering to a patient in need of such treatment an effective amount of a compound as claimed in claim 1.

* * * * *